Figure 1:
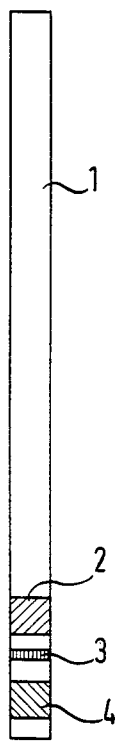

United States Patent [19]

Deneke et al.

[11] Patent Number: 4,563,422

[45] Date of Patent: Jan. 7, 1986

[54] METHOD AND COMPOSITION FOR THE REMOVAL OF ASCORBIC ACID FROM AQUEOUS LIQUIDS

[75] Inventors: Ulfert Deneke, Mörlenbach; Hans Lange, Lampertheim; Walter Rittersdorf, Mannheim-Waldhof, all of Fed. Rep. of Germany

[73] Assignee: Boehringer Mannheim GmbH, Mannheim-Waldhof, Fed. Rep. of Germany

[21] Appl. No.: 380,804

[22] Filed: May 21, 1982

Related U.S. Application Data

[63] Continuation of Ser. No. 135,378, Mar. 28, 1980, abandoned.

[30] Foreign Application Priority Data

Apr. 10, 1979 [DE] Fed. Rep. of Germany ....... 2914487

[51] Int. Cl.⁴ ............................ C12Q 1/30; C12Q 1/28
[52] U.S. Cl. .......................................... 435/27; 435/28; 435/805; 435/810; 436/93; 436/175
[58] Field of Search ............... 435/14, 25, 28, 805, 435/810, 27; 426/10, 12; 436/93, 175

[56] References Cited

U.S. PATENT DOCUMENTS

| | | | |
|---|---|---|---|
| 3,802,842 | 4/1974 | Lange et al. | 435/14 |
| 3,926,732 | 12/1975 | Rosen et al. | 435/14 |
| 3,992,158 | 11/1976 | Przyblowicz et al. | 435/14 |
| 4,160,008 | 7/1979 | Fenocketti et al. | 435/14 |
| 4,168,205 | 9/1979 | Danninger et al. | 435/14 |
| 4,314,030 | 2/1982 | Habich | 435/14 |

*Primary Examiner*—Benoit Castel
*Attorney, Agent, or Firm*—Felfe & Lynch

[57] ABSTRACT

The present invention provides a process for removing ascorbic acid from aqueous solutions by the addition of ascorbate oxidase, wherein catalase and hydrogen peroxide are also added to the solution.

The present invention also provides an agent for the removal of ascorbic acid from aqueous solutions, based on a solid carrier material impregnated with ascorbate oxidase, wherein the carrier material also contains catalase and hydrogen peroxide and optionally also a stabilizer and/or buffer substance.

19 Claims, 2 Drawing Figures

U.S. Patent     Jan. 7, 1986     4,563,422

METHOD AND COMPOSITION FOR THE REMOVAL OF ASCORBIC ACID FROM AQUEOUS LIQUIDS

This is a continuation of Ser. No. 135,378 filed Mar. 28, 1980, now abandoned.

The present invention is concerned with a process for the removal of ascorbic acid from aqueous solutions and with an agent for carrying out this process.

Ascorbic acid is frequently present in aqueous liquids and especially in aqueous solutions of physiological origin, as well as in plant juices and the like. As is known, ascorbic acid is a strong reducing agent which, under certain circumstances, can have a disturbing effect especially when other components of the aqueous liquids are to be analytically determined. Thus, for example, in the case of the analysis of urine for pathological components, ascorbic acid can have a very disturbing effect. Many methods of determination and especially rapid diagnostics for the determination of glucose, blood, nitrite, urobilinogen and bilirubin, are more or less strongly disturbed by ascorbic acid in the sense of a simulation of lower concentrations. On the other hand, in the case of Fehling's test for glucose, the presence thereof is simulated by ascorbic acid so that falsely positive or too high values are obtained.

Since the presence of ascorbic acid in urine due to a liberal alimentary ingestion thereof is very common, various attempts have already been made to remove ascorbic acid from urine prior to analysis for the particular components which it is desired to determine. Thus, the following processes are known:
 oxidation with iodine solution and removal of excess iodine with thiosulphate solution,
 oxidation with manganese dioxide and filtering off nonconsumed oxidation agent,
 oxidation with alkaline hydrogen peroxide, and treatment of the urine with an anion exchanger.

All these processes require a laborious treatment of the urine so that they have not established themselves in practice. Furthermore, under certain circumstances, the materials to be detected are either destroyed or simulated.

Test papers are also known in which the urine must first be chromatographed through a zone containing an oxidizing agent or an anion exchanger (see Federal Republic of Germany Patent Specification No. 1,598,008), the ascorbic acid thereby being removed, whereafter the urine passes to the actual reagent zone where reaction can take place without disturbance. Test papers of this kind are commercially available for glucose and galactose. However, they have a complicated structure. In addition, the time needed for carrying out the test is considerably increased due to the necessary chromatographing time.

According to one of our previous proposals, it is already known to remove ascorbic acid by the addition of ascorbate oxidase (see Federal Republic of Germany Patent Specification No. 2,625,834). This process is certainly useful but, for the removal of the disturbance, especially when there is a possibility that comparatively large amounts of ascorbic acid may be present, it is necessary to use a large amount of ascorbate oxidase. Therefore, for many cases, the use of this process or of test papers working according to this process is uneconomical due to the large amount of ascorbate oxidase which is necessary. A further disadvantage of this process is that the solution from which the ascorbic acid must be removed must be vigorously shaken in order that the oxygen necessary for the reaction goes into solution.

Therefore, it is an object of the present invention to provide a process for the removal of ascorbic acid from aqueous liquids which avoids the above-described disadvantages of the known processes and agents and can be carried out quickly, dependably and without the use of special adjuvants and is economically acceptable.

Thus, according to the present invention, there is provided a process for the removal of ascorbic acid from aqueous solutions by the addition of ascorbate oxidase, wherein catalase and hydrogen peroxide are additionally added to the solution.

The process according to the present invention permits a rapid and certain removal of ascorbic acid from aqueous solutions, such as urine. This is surprising because an evolution of oxygen takes place in the solution which far exceeds the solubility of oxygen in the aqueous liquid so that it was to have been expected that the greater part of the oxygen formed would be lost due to the evolution of gas. Furthermore, a negative influence of the hydrogen peroxide on the position of the equilibrium of the reaction was to have been expected since, in the case of many investigations, hydrogen peroxide is found as the end product of the oxidation of ascorbic acid by ascorbate oxidase. Unexpectedly, however, according to the present invention, with the same amount of ascorbate oxidase, much greater amounts of ascorbic acid can be destroyed than in the case of absence of hydrogen peroxide and catalase or the amount of ascorbate oxidase needed for the removal of a definite amount of ascorbic acid can be substantially reduced.

Furthermore, it is especially surprising that this process can even be used when, subsequently, a reaction is carried out in which the hydrogen peroxide formed represents a measurement parameter. This is, for example, the case in the determination of glucose with glucose oxidase, with the measurement of the hydrogen peroxide formed with 4-aminophenazone and phenol.

According to the process of the present invention, the catalase is preferably used in the form of a commercially available preparation. Hydrogen peroxide can be used as such but it is preferred to employ it in the form of a solid adduct, i.e. an addition compound of hydrogen peroxide on to another substance, preferred examples thereof including perborates, urea perhydrate and mannitol perhydrate.

The present invention also provides an agent for the removal of ascorbic acid from aqueous liquids, based upon a solid carrier material impregnated with ascorbate oxidase, wherein the carrier material also contains catalase and hydrogen peroxide and optionally also a stabilizing and/or buffer substance.

The carrier materials can be inert substances which can be impregnated with ascorbate oxidase, catalase and hydrogen peroxide or a solid hydrogen peroxide adduct and are preferably carrier materials of the kind known for the production of test strips. Typical examples thereof include absorbent papers and paper-like materials based upon natural, synthetic and artificial fibers, fleeces, open-celled foamed materials and porous glass or upon fiber mats and the like made of inorganic materials, such as glass.

The carrier material either contains the reagents individually, i.e. in zones spatially separated from one another, or contains a mixture of the enzymes separated from the hydrogen peroxide, this latter embodiment being preferred since we have, surprisingly, found that the two enzymes, ascorbate oxidase and catalase, have a mutually stabilizing effectiveness and thus the storage stability of the impregnated material is substantially improved. Therefore, it is possible to provide the two enzymes together on the carrier material without using additional stabilizers. However, it is preferred also to incorporate into the carrier material conventional enzyme stabilizers and/or buffer substances which provide the pH value suitable for the stability of these enzymes.

The hydrogen peroxide which, as mentioned above, is preferably present in the carrier material in the form of a solid adduct, is preferably also stabilized, conventional hydrogen peroxide stabilizers thereby preferably being used. Very good stabilizing results have been achieved with the use of pectin, polyvinylpyrrolidone and dextran and with mixtures thereof.

The production of the impregnated carrier material can be carried out very simply by impregnating the material with a solution of the substance or mixture of substances to be applied and then dried. Thus, for example, an appropriate paper is impregnated and ascorbate oxidase, catalase, stabilizer and buffer material and dried and another carrier material is impregnated with a solution of a hydrogen peroxide adduct, which preferably also contains a stabilizing agent, and dried in the same way. Appropriately dimensioned pieces of the impregnated carrier materials produced in this manner can then be fixed to an appropriate substrate carrier material, for example by adhesion. In this way, an agent is obtained of the above-described kind which has a first compact carrier material on to which is fixed at least one second porous, absorbent carrier material which is impregnated with one or more of the above-mentioned active materials. The first compact material is preferably in the form of a strip or rod. Then, for example, such a rod can be dipped into an ascorbic acid-containing solution so that the reagents are dissolved from the porous second carrier material and the reagents mixed by simply stirring, the first compact material thereby serving as a handle, in order to speed up the course of the reaction. Such rodlets or strips suitable for stirring up are frequently referred to as "plungers". The compact first carrier material can consist of any desired inert material, glass or synthetic resins being preferred. Thus, for example, a synthetic resin rodlet as first compact carrier material can have stuck on to it two paper strips, one of which is impregnated with ascorbate oxidase and catalase and the other with hydrogen peroxide. The plunger thus obtained is then dipped into the aqueous liquid, for example urine, and briefly stirred, the reagents thereby being dissolved off and well mixed up and completely destroying the ascorbic acid in a short time.

When the agent according to the present invention contains a buffer substance, then it is preferable to use one which can maintain a pH value of from 5 to 8.5. Especially preferred buffer substances include tris-citrate buffer and/or tris-citric acid buffer, the latter being especially preferred when a solid hydrogen peroxide adduct is present which has a strongly alkaline reaction.

The amount of reagents in the agent according to the present invention is, in the first place, determined by the intended purpose of use. If it is to be used as a plunger for the removal of ascorbic acid from urine samples, then it is preferable for the amount of ascorbate oxidase to be at least 30 U and more preferably from 35 to 40 U. For other aqueous liquids, for example fruit juices, the amounts are selected according to the expected content of ascorbic acid.

Figure 2:
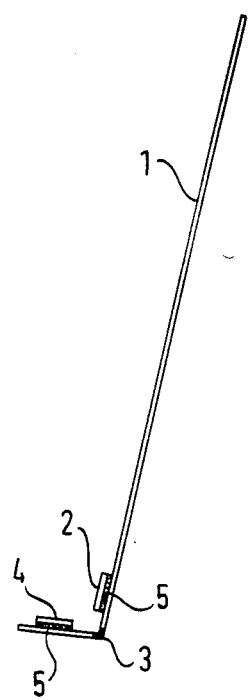

For a better understanding of the present invention, reference will be made to the accompanying drawings, in which:

FIG. 1 is a front view of an agent according to the present invention for the removal of ascorbic acid in aqueous liquids; and FIG. 2 is a side view of the agent according to FIG. 1.

The embodiment of the agent according to the present invention illustrated in FIGS. 1 and 2 of the accompanying drawings is constructed as a "plunger". A strip 1 of synthetic resin, which represents the first compact carrier material, carries, close to its lower end, a paper strip 2 impregnated with 35 $\mu$mol of hydrogen peroxide and a paper strip 4 impregnated with 36 U ascorbate oxidase and 10,000 U catalase. Between the two paper strips 2 and 4, there is a color-marked bending point 3. By bending at the bending point, the synthetic resin strip is given the form of a good-stirring spatula. The two porous absorbent carriers 2 and 4 are fixed to the synthetic resin strip 1 by means of adhesive 5.

The present invention can be used for body fluids, such as urine, serum and plasma, as well as for other ascorbate-containing aqueous liquids, for example fruit juices and other plant juices.

The following Examples are given for the purpose of illustrating the present invention:

EXAMPLE 1

Removal of large amounts of ascorbate from urine with and without shaking

A urine sample is made up with ascorbic acid to a content of 20 mg. ascorbate per 100 ml. 10 ml. amounts of this sample are mixed with 10 U ascorbate oxidase. One sample is gently mixed up and, after standing for 10 minutes, the content of ascorbate is determined. 67% of the added ascorbate are still found. The other sample is vigorously shaken for 10 minutes. After this time, no ascorbate can be detected in it. In two further samples, to which no ascorbate oxidase is added, with and without shaking, there is found, after 10 minutes, practically all of the added ascorbic acid.

EXAMPLE 2

Introduction of oxygen by means of hydrogen peroxide and catalase

A urine sample is made up with ascorbic acid to 50 mg. of ascorbate per 100 ml. 10 ml. amounts of this urine are mixed with 10 U ascorbate oxidase and 10,000 U catalase. Subsequently, 6 mMol of hydrogen peroxide are added thereto, followed by brief stirring. After 10 minutes, the content of residual ascorbate is determined. No more ascorbate can be found. In a further sample, to which no hydrogen peroxide has been added but only ascorbate oxidase and catalase, there is still found 80% of the added ascorbate.

EXAMPLE 3

Production of an ascorbate oxidase spatula (a) Preparation of impregnation solution 1

83,000 U (10,000 to 160,000 U) ascorbate oxidase, 83 mio U (40 to 160 mio U) catalase, 15 g. mannitol and 0.2 mol/liter each of tris and citrate (pH 7.6) are dissolved in water and the solution made up to 100 ml. with water. A suitable paper is impregnated with this solution. After drying, the paper is cut up into 6 mm. wide strips, which are stuck on to a synthetic resin carrier. After cutting again, the 6×6 mm. zones obtained each contains 36 U ascorbate oxidase and 10,000 U (5000 to 15,000 U) catalase.

(b) Preparation of impregnation solution 2

Solution A: 5 g. pectin are dissolved in 100 ml. double distilled water.

Solution B: 33.4 g. collidon 25 and 66.6 ml. water are mixed.

Solutions A and B are mixed together and 40 g. urea perhydrate and 50 g. collidon 25 are dissolved therein. A suitable paper is impregnated with this solution and cut up into 6 mm. wide strips. These strips are stuck on to the same synthetic resin carrier which already contains the ascorbate oxidase-containing paper. After cutting, the resultant 6×6 mm. test zones each contain 60 (50 to 100) μmol urea perhydrate.

Between the ascorbate oxidase test zone and the urea perhydrate test zone, the synthetic resin carrier has a bending point which is bent before use in order to produce a stirrer spatula. With this so formed spatula, 10 ml. of a urine, which contains 50 mg. ascorbic acid/100 ml., is briefly stirred and the spatula left for 10 minutes in the urine. After 10 minutes, the spatula is removed and the residual content of ascorbic acid determined. Ascorbate can no longer be detected. The thus treated urine can be used for testing, without disturbance, by means of test rods, for nitrite, pH value, protein, glucose, ketone bodies, bilirubin, urobilinogen and blood.

EXAMPLE 4

Removal of ascorbate from orange juice

With the carrier described in Example 3, 10 ml. of an orange juice with a content of 350 mg. ascorbate/liter can be trested in the same manner as described in Example 3. Here, too, thereafter no ascorbate can be detected.

EXAMPLE 5

15 ml. Urine, containing 150 to 250 mg./100 ml. glucose and 50 mg./100 ml. ascorbate, were tested with test strips according to Example 8 of Federal Republic of Germany Patent Specification No. 2,625,834. The reaction is negative since the ascorbate results in a complete suppression. Subsequently, the urine is stirred with the spatula according to the above Example 3, the ascorbic acid thereby being removed. When again testing for glucose with the above-mentioned test strip, there is obtained an appropriate signal. This is surprising because it was to have been expected that the catalase would have destroyed the hydrogen peroxide formed in the detection of the glucose.

EXAMPLE 6

Ascorbate disturbs photometric glucose determinations which depend upon the reaction with GOD, POD, phenol and 4-aminophenazone. Therefore, the spatula is also used for the removal of ascorbate from samples for the glucose determination by the GOD-PAP method. For this purpose, 15 ml. urine are treated with the spatula described in Example 3 and, in this way, freed from up to 50 mg. ascorbate. Subsequently, 0.02 ml. of this urine are introduced into 3 ml. of the following reagent mixture:

| phosphate buffer | 0.12 mMol/liter, pH 7.0 |
|---|---|
| POD | 1.5 U/ml. |
| GOD | 19 U/ml. |
| 4-aminophenazone | 0.92 mMol/l. |
| phenol | 11 mMol/l. |

Before adding the sample, $E_1$ is determined. After addition of the sample, the mixture is incubated for 40 minutes and $E_2$ is then determined. A glucose standard is measured in the same way and from this the glucose content of the urine is determined. By means of the treatment of the sample urine with catalase, up to 1000 U/ml. of catalase can be used in the above photometric test without disturbance of the test occurring.

It will be understood that the specification and examples are illustrative, but not limitative of the present invention and that other embodiments within the spirit and scope of the invention will suggest themselves to those skilled in the art.

What is claimed is:

1. Process for removing ascorbic acid from an aqueous solution containing same which process comprises adding to the aqueous solution, ascorbate oxidase, catalase and hydrogen peroxide, the catalase being added simultaneously with, or prior to the addition of hydrogen peroxide.

2. Process as claimed in claim 1 wherein the hydrogen peroxide is used in the form of a hydrogen peroxide-containing adduct.

3. Process as claimed in claim 2 wherein said adduct is a perborate.

4. Process as claimed in claim 2 wherein said adduct is a urea perhydrate.

5. Process as claimed in claim 2 wherein said adduct is a mannitol perhydrate.

6. Reagent for the removal of ascorbic acid from aqueous solutions comprising a solid carrier material impregnated with ascorbate oxidase, wherein the carrier material also contains catalase and hydrogen peroxide.

7. Reagent as claimed in claim 6 wherein said carrier material additionally contains a stabilizer.

8. Reagent as claimed in claim 7 wherein said stabilizer is pectin, polyvinylpyrrolidone or dextran, or mixtures thereof.

9. Reagent as claimed in claim 6 wherein said carrier material additionally contains a buffer substance.

10. Reagent as claimed in claim 6 wherein said carrier material contains the ascorbate oxidase and the catalase together and the hydrogen peroxide physically separated therefrom.

11. Reagent as claimed in claim 6 wherein said hydrogen peroxide is present as a solid adduct.

12. Reagent as claimed in claim 6 wherein said carrier material consists of the first compact carrier material to which is fixed at least one second porous absorbent carrier material which is impregnated with one or more of the active materials.

13. Reagent as claimed in claim 12 wherein the first carrier material is in the form of a strip or rod.

14. Reagent as claimed in claim 12 wherein the first carrier material consists of glass or synthetic resin.

15. Reagent as claimed in claim 12 wherein the second carrier material is a paper or fleece.

16. Reagent as claimed in claim 6 wherein said carrier material contains a buffer substance which is effective at a pH value of from 5 to 8.5.

17. Reagent as claimed in claim 16 wherein said buffer substance is tris-citrate or tris-citric acid buffer.

18. Reagent as claimed in claim 16 containing at least 30 U of ascorbate oxidase.

19. Reagent as claimed in claim 18 containing 35 to 40 U of ascorbate oxidase.

* * * * *